US011331466B2

(12) United States Patent
Keen et al.

(10) Patent No.: US 11,331,466 B2
(45) Date of Patent: May 17, 2022

(54) INFLOW CANNULA INCLUDING EXPANDABLE SLEEVE AND METHODS OF IMPLANTING SAME

(71) Applicant: TC1 LLC, St. Paul, MN (US)

(72) Inventors: Rachel Keen, Medford, MA (US); Steve Franklin, Haverhill, MA (US); Tracee Eidenschink, Wayzata, MN (US); Ted Dale, Corcoran, MN (US); Gary Erzberger, Plymouth, MN (US); Kristopher Vietmeier, Monticello, MN (US); Julien Duhamel, Chelmsford, MA (US); Francheska Torres, Charlton, MA (US)

(73) Assignee: TC1 LLC, St. Paul, MN (US)

( * ) Notice: Subject to any disclaimer, the term of this patent is extended or adjusted under 35 U.S.C. 154(b) by 189 days.

(21) Appl. No.: 16/745,008

(22) Filed: Jan. 16, 2020

(65) Prior Publication Data
US 2020/0276370 A1 Sep. 3, 2020

Related U.S. Application Data

(60) Provisional application No. 62/811,814, filed on Feb. 28, 2019.

(51) Int. Cl.
A61M 25/14 (2006.01)
A61M 60/148 (2021.01)
A61M 60/419 (2021.01)
A61M 60/857 (2021.01)
A61M 60/165 (2021.01)
A61M 25/04 (2006.01)

(52) U.S. Cl.
CPC ........ A61M 60/148 (2021.01); A61M 60/165 (2021.01); A61M 60/419 (2021.01); A61M 60/857 (2021.01); A61M 25/04 (2013.01)

(58) Field of Classification Search
CPC .............. A61M 60/148; A61M 60/419; A61M 60/857; A61M 60/165; A61M 25/04
USPC .......................................... 600/16
See application file for complete search history.

(56) References Cited

U.S. PATENT DOCUMENTS 8,152,845 B2 4/2012 Bourque
8,579,790 B2 11/2013 Jeffery et al.
(Continued)

OTHER PUBLICATIONS

International Search Report and Written Opinion for International Patent Application No. PCT/US2020/013803, dated Apr. 2, 2020, 18 pages.

*Primary Examiner* — Erin M Piateski
(74) *Attorney, Agent, or Firm* — Armstrong Teasdale LLP

(57) ABSTRACT

Disclosed herein is an inflow cannula for an implantable blood pump assembly. The inflow cannula includes a tubular body that extends from a proximal end to a distal end. The tubular body includes a proximal portion adapted for connection to a pump housing, and a distal portion adapted for positioning within an opening formed in a heart. The inflow cannula further includes an expandable sleeve coupled to an exterior surface of the distal portion. The sleeve has a first portion coupled to the distal portion of the tubular body, and a second portion extending from the distal end of the tubular body. The second portion is deployable from a first, stored configuration to a second, deployed configuration in which the second portion expands radially to engage and conform to an endocardial surface of the heart.

19 Claims, 7 Drawing Sheets

(56) References Cited

U.S. PATENT DOCUMENTS

| | | | |
|---|---|---|---|
| 8,870,739 B2 | 10/2014 | Larose et al. | |
| 9,387,278 B2 | 7/2016 | Miyakoshi et al. | |
| 9,981,076 B2 | 5/2018 | Callaway et al. | |
| 2002/0082467 A1 | 6/2002 | Campbell | |
| 2006/0178551 A1* | 8/2006 | Melvin | A61M 60/268 |
| | | | 600/16 |
| 2007/0299297 A1* | 12/2007 | Jarvik | A61L 33/022 |
| | | | 600/16 |
| 2011/0124950 A1* | 5/2011 | Foster | A61M 60/205 |
| | | | 600/16 |
| 2012/0143141 A1* | 6/2012 | Verkaik | A61M 60/00 |
| | | | 604/175 |
| 2013/0060267 A1 | 3/2013 | Farnan et al. | |
| 2018/0214619 A1* | 8/2018 | Cook | A61M 60/857 |

\* cited by examiner

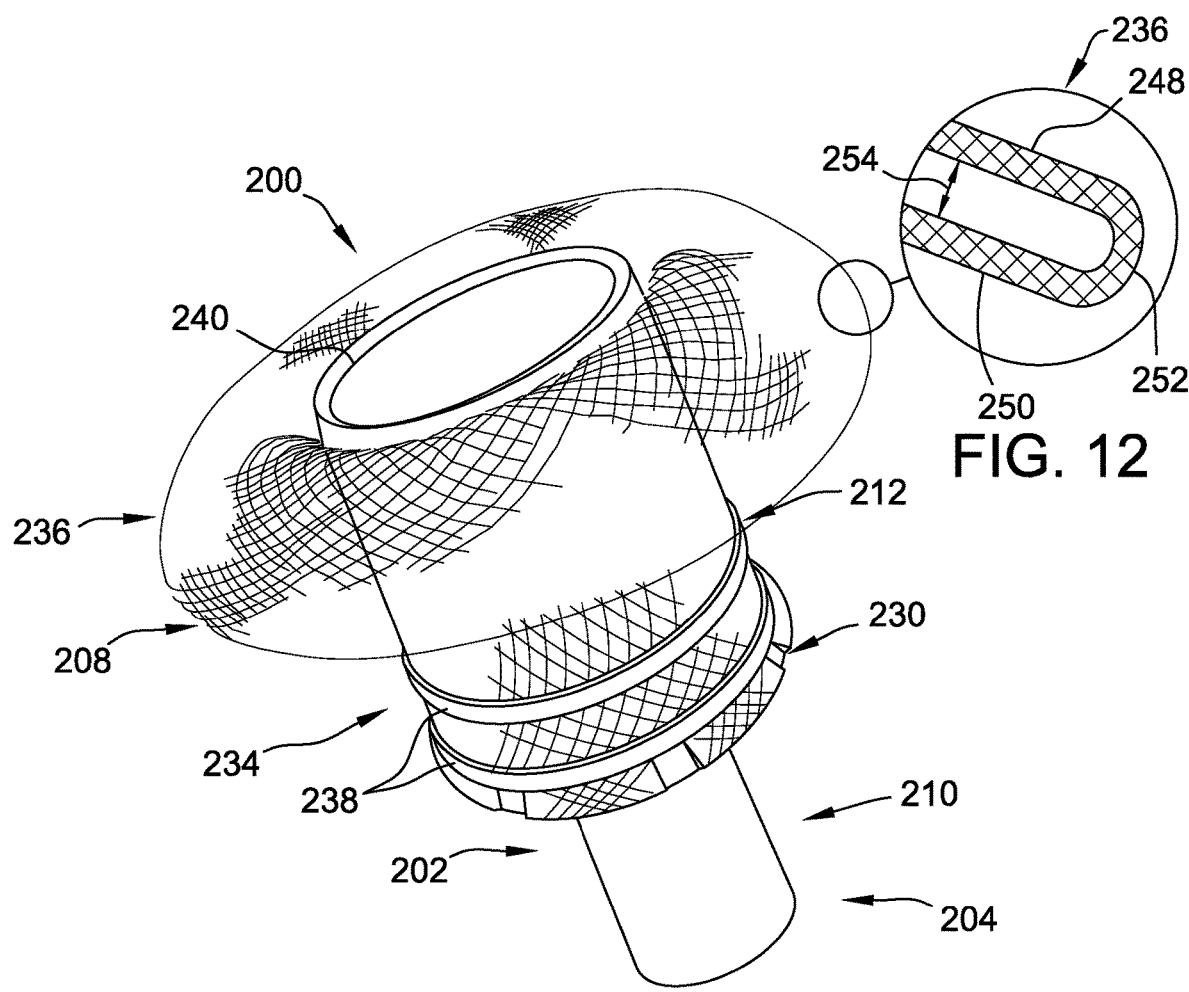
FIG. 12
FIG. 9
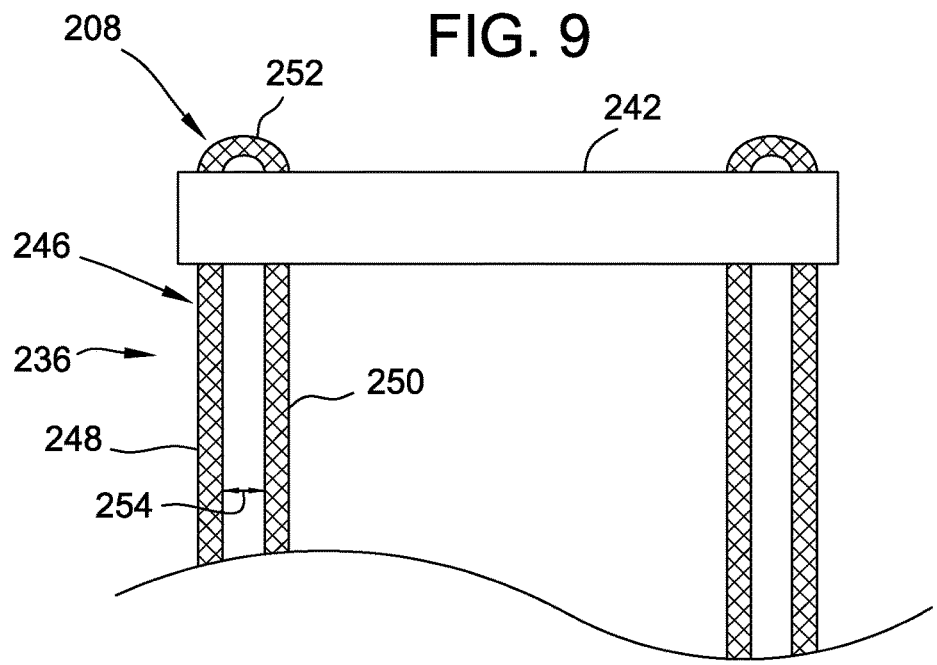
FIG. 10

INFLOW CANNULA INCLUDING EXPANDABLE SLEEVE AND METHODS OF IMPLANTING SAME

CROSS-REFERENCE TO RELATED APPLICATIONS

This application claims priority to U.S. Provisional Patent Application Ser. No. 62/811,814, filed on Feb. 28, 2019, the disclosure of which is hereby incorporated by reference in its entirety.

BACKGROUND OF THE DISCLOSURE a. Field of the Disclosure

The present disclosure relates generally to mechanical circulatory support systems, and more specifically relates to inflow cannulas of blood pump assemblies that include an expandable sleeve configured to alleviate risks associated with stasis or areas of low blood flow around the inflow cannula.

b. Background

Ventricular assist devices, known as VADs, are implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

In certain applications, an inflow cannula of the VAD is implanted within the left ventricle of a patient's heart to supply blood from within the ventricle to a pump of the VAD. In some instances, blood flow around the inflow cannula may be reduced, resulting in areas of low blood flow or stasis. These areas of low blood flow and stasis, in combination with prothrombotic myocardium tissue around the hole formed in the patient's heart, are potential sites of thrombus formation within the ventricle.

Accordingly, a need exists for improved inflow cannulas for VADs that reduce or eliminate areas of low blood flow or stasis around the inflow cannula.

SUMMARY OF THE DISCLOSURE

The present disclosure is directed to an inflow cannula for an implantable blood pump assembly. The inflow cannula includes a tubular body that extends from a proximal end to a distal end. The tubular body includes a proximal portion adapted for connection to a pump housing, and a distal portion adapted for positioning within an opening formed in a heart. The inflow cannula further includes an expandable sleeve coupled to an exterior surface of the distal portion. The sleeve has a first portion coupled to the distal portion of the tubular body, and a second portion extending from the distal end of the tubular body. The second portion is deployable from a first, stored configuration to a second, deployed configuration in which the second portion expands radially to engage and conform to an endocardial surface of the heart.

The present disclosure is further directed to an implantable blood pump assembly that includes a housing, a rotor, a stator, and an inflow cannula. The housing defines an inlet, an outlet, and a flow path extending from the inlet to the outlet. The rotor is positioned within the flow path and is operable to pump blood from the inlet to the outlet. The stator is positioned within the pump housing and is operable to drive the rotor. The inflow cannula has a proximal portion adapted for coupling to the housing inlet, and a distal portion opposite the proximal portion. The implantable blood pump assembly further includes an expandable sleeve coupled to an exterior of the distal portion of the inflow cannula. The sleeve has a first portion coupled to the distal portion of the inflow cannula, and a second portion extending from a distal end of the inflow cannula. The second portion is deployable from a first, stored configuration to a second, deployed configuration in which the second portion expands radially to engage and conform to an endocardial surface of a heart.

The present disclosure is further directed to a method for implanting an inflow cannula within a heart of patient. The method includes positioning a distal portion of the inflow cannula within a hole formed in the heart. The inflow cannula includes an expandable sleeve that has a first portion coupled to the distal portion of the inflow cannula, and a second portion extending from a distal end of the inflow cannula. The method further includes securing the inflow cannula to the heart, and deploying the second portion of the sleeve from a first, stored configuration to a second, deployed configuration such that the second portion of the sleeve expands radially and engages and conforms to an endocardial surface of the heart.

BRIEF DESCRIPTION OF THE DRAWINGS

FIGS. 7-9 are perspective views of the inflow cannula shown in FIG. 5, illustrating the expandable sleeve transitioning from a stored configuration, shown in FIG. 7, to a transitional state, shown in FIG. 8, between the stored configuration and the deployed configuration, to the deployed configuration, shown in FIG. 9.

FIG. 10 is an enlarged schematic sectional view of a distal end of the expandable sleeve of FIG. 5, shown in the stored configuration.

FIG. 12 is an enlarged schematic sectional view of a distal end of the expandable sleeve of FIG. 9, shown in the deployed configuration.

DETAILED DESCRIPTION OF THE DISCLOSURE

The present disclosure is directed to implantable blood pump assemblies and, more specifically, to inflow cannulas of implantable blood pump assemblies that are configured to reduce potential areas of thrombus formation within the heart following implantation of the blood pump assembly. In particular, embodiments of the inflow cannulas disclosed herein include an expandable sleeve configured to occupy or fill the space around the distal end of the inflow cannula that is positioned within a ventricle of the heart. The area occupied by the expandable sleeve might otherwise be associated with areas of low blood flow or stasis. By occupying this space, the expandable sleeve is positioned to capture or trap thrombi formed on the endocardial tissue beneath the sleeve, thereby preventing the thrombi from detaching and being released into a patient's blood stream. Additionally, embodiments of the expandable sleeves disclosed herein provide a smooth contour along the endocardial surface of the heart, and fill gaps or spaces between the distal end of the inflow cannula and the endocardial surface, thereby avoiding sharp corners or curves at the interface between the inflow cannula and endocardial wall that might otherwise result in low blood flow or stasis. The inflow cannulas of the present disclosure thereby facilitate reducing areas of low blood flow or stasis along the distal end of the inflow cannula. Additionally, embodiments of the expandable sleeves are constructed from materials that promote tissue reendothelialization along the endocardial surface, and thereby facilitate faster healing of a patient following an implant procedure.

Further, embodiments of the expandable sleeves disclosed herein have a flexible, yet resilient construction such that, when the sleeve is deployed, the sleeve is biased or forced outward against the endocardial surface of the heart. The expandable sleeves thereby facilitate preventing tissue from occluding or growing over the flow path opening at the distal end of the inflow cannula, and maintaining an open flow path through the inflow cannula. Further, by reducing the risk of tissue overgrowth, the expandable sleeves of the present disclosure facilitate reducing or minimizing the length that the inflow cannula protrudes into the heart ventricle.

Figure 1:
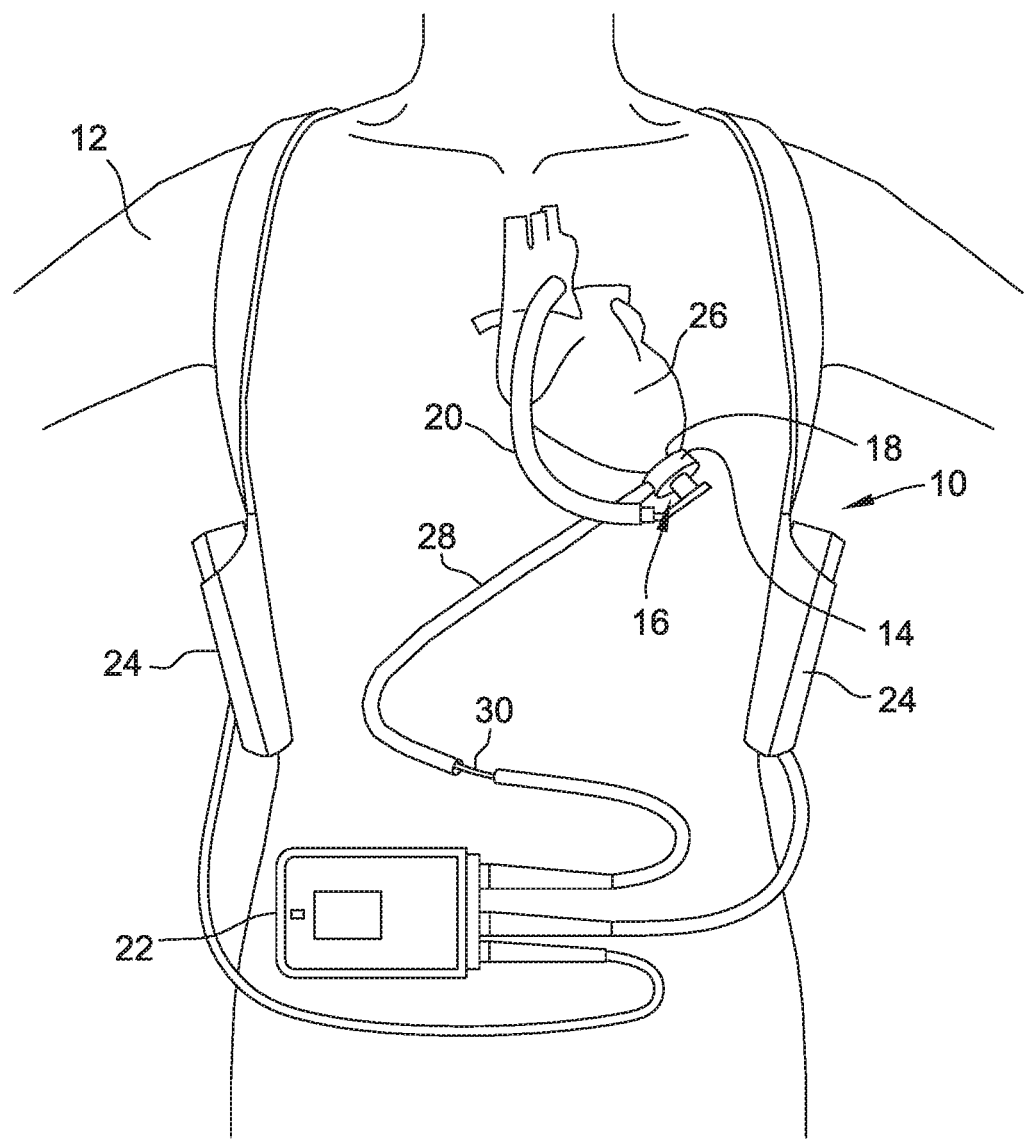
FIG. 1 is an illustration of a mechanical circulatory support system implanted in a patient's body.

Referring now to the drawings, FIG. 1 is an illustration of a mechanical circulatory support system 10 implanted in a patient's body 12. The mechanical circulatory support system 10 includes an implantable blood pump assembly 14 that includes a blood pump 16, a ventricular cuff 18, and an outflow cannula 20. The mechanical circulatory support system 10 also includes an external system controller 22 and one or more power sources 24.

Figure 2:
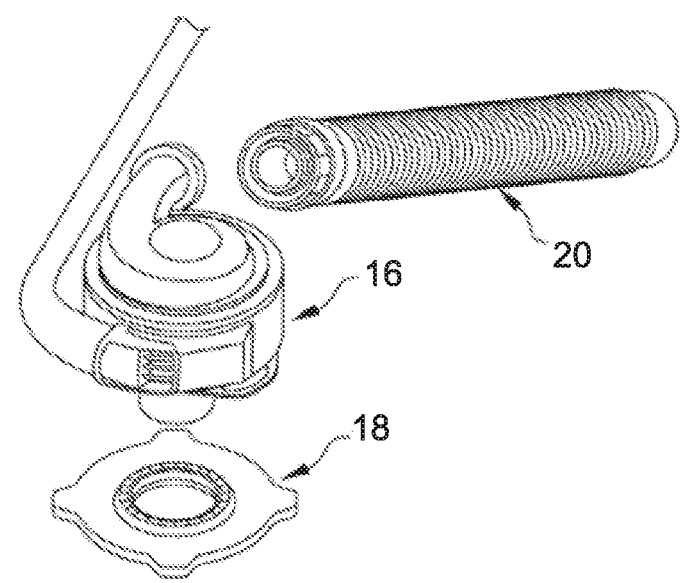
FIG. 2 is an exploded view of certain components of the circulatory support system shown in FIG. 1.

The blood pump assembly 14 can be implemented as or can include a ventricular assist device (VAD) that is attached to an apex of the left ventricle, as illustrated, or the right ventricle, or both ventricles of the heart 26. With additional reference to FIG. 2, the blood pump assembly 14 can be attached to the heart 26 via the ventricular cuff 18 which is sewn to the heart 26 and coupled to the blood pump assembly 14, as described further herein. The other end of the blood pump assembly 14 connects to the ascending or descending aorta via the outflow cannula 20 so that the blood pump assembly 14 effectively diverts blood from the weakened ventricle and propels it to the aorta for circulation to the rest of the patient's vascular system. The VAD can include a centrifugal (as shown) or axial flow pump as described in further detail herein that is capable of pumping the entire output delivered to the left ventricle from the pulmonary circulation (i.e., up to 10 liters per minute).

FIG. 1 illustrates the mechanical circulatory support system 10 during battery powered operation. A communication line 28 connects the implanted blood pump assembly 14 to the external system controller 22, which monitors system 10 operation. In the illustrated embodiment, the communication line 28 is shown as a driveline that exits through the patient's abdomen 30, although it should be understood that the blood pump assembly 14 may be connected to the external system controller 22 via any suitable communication line, including wired and/or wireless communication. The system can be powered by either one, two, or more batteries 24. It will be appreciated that although the system controller 22 and power source 24 are illustrated outside/external to the patient body, the communication line 28, system controller 22 and/or power source 24 can be partially or fully implantable within the patient, as separate components or integrated with the blood pump assembly 14.

Figure 3:
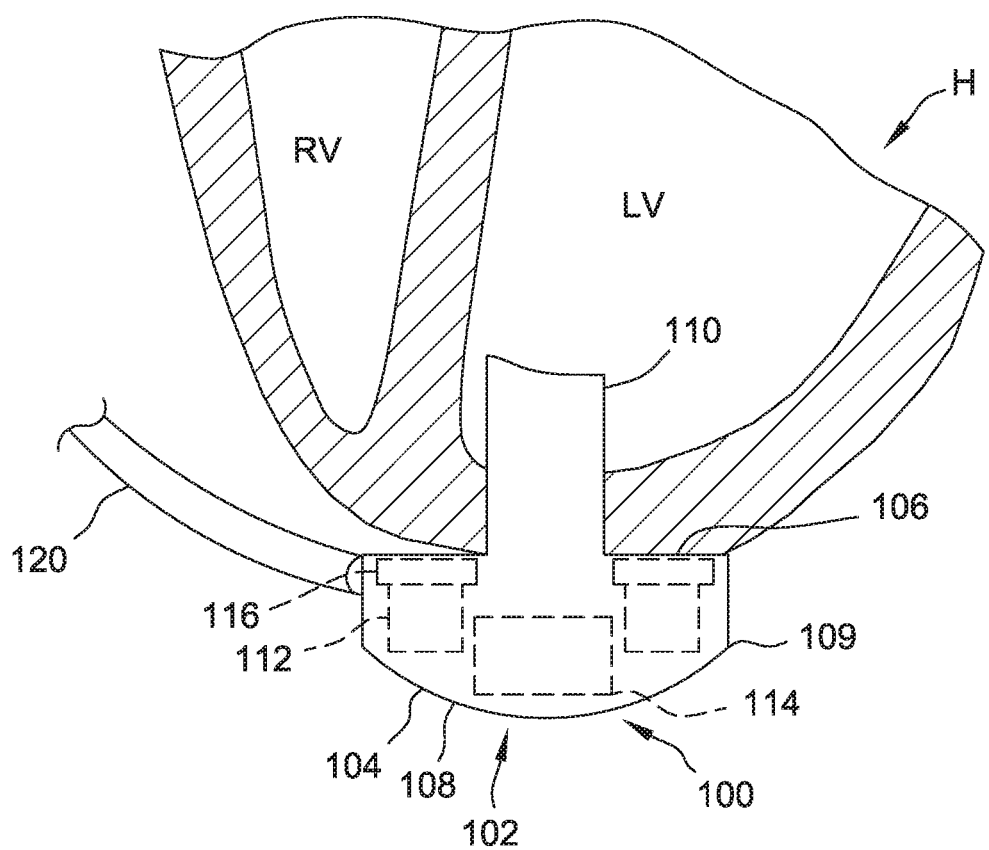
FIG. 3 is an illustration of a blood pump assembly suitable for use in the mechanical circulatory support system of FIG. 1, the blood pump assembly shown in an operational position implanted in a patient's body.
Figure 4:
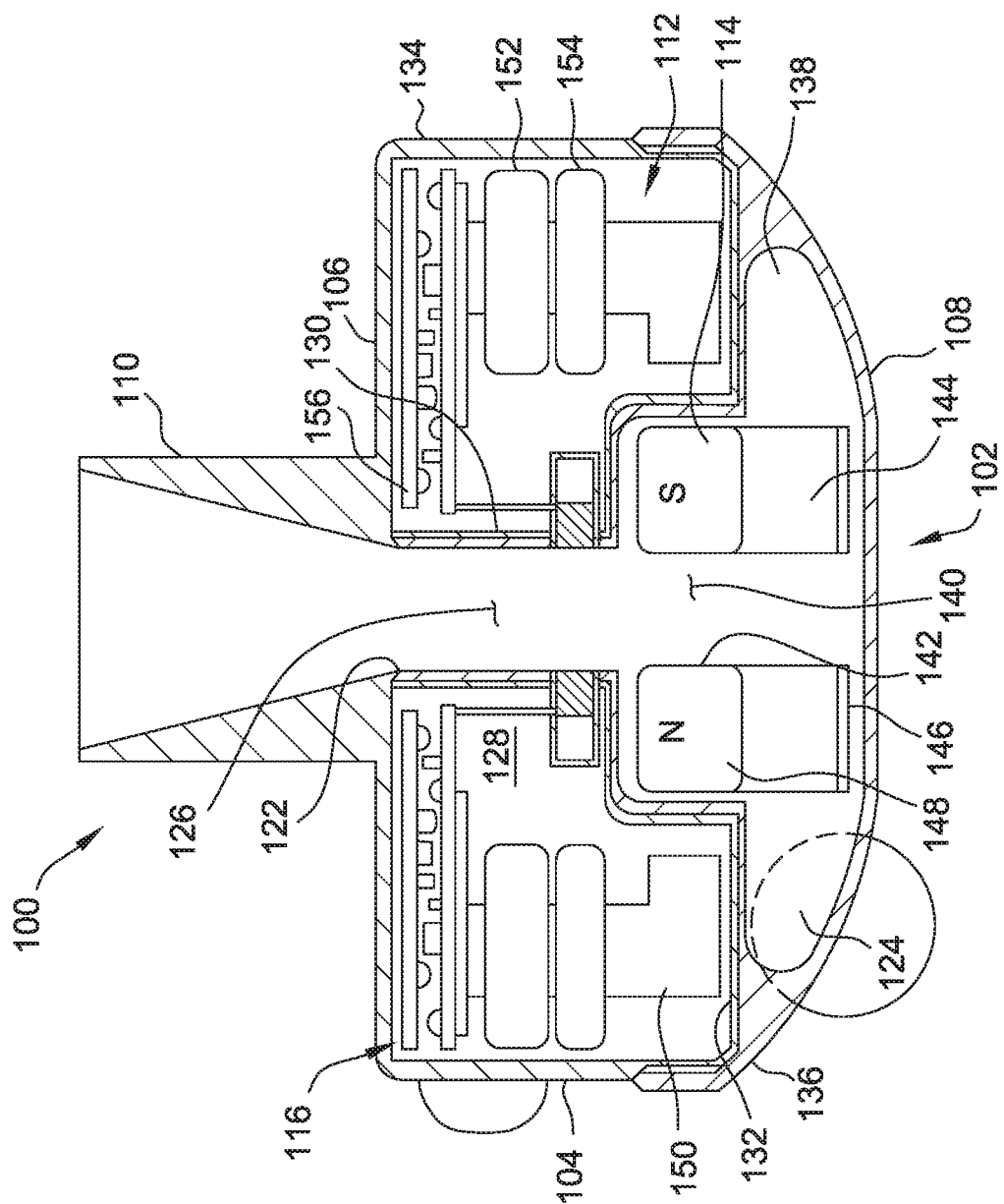
FIG. 4 is a schematic cross-sectional view of the blood pump assembly of FIG. 3.

FIG. 3 is an illustration of an implantable blood pump assembly 100 suitable for use in the mechanical circulatory support system 10 of FIG. 1, where the blood pump assembly 100 is shown in an operational position implanted in a patient's body. FIG. 4 is a schematic cross-sectional view of the blood pump assembly 100 of FIG. 3. In the illustrated embodiment, the blood pump assembly 100 is a left ventricular assist blood pump assembly connected to the left ventricle LV of the heart H.

The blood pump assembly 100 includes a blood pump 102 including a circular shaped housing 104 having a first outer face or wall 106 and a second outer face or wall 108. The blood pump assembly 100 further includes an inflow cannula 110 (generally, an inlet conduit) that, in the illustrated embodiment, extends from the first outer wall 106 of the pump housing 104. When the blood pump assembly 100 is implanted into a patient's body, as shown in FIG. 3, the first outer wall 106 of the housing 104 is positioned against the patient's heart H, and the second outer wall 108 of the housing 104 faces away from the heart H. The inflow cannula 110 extends into the left ventricle LV of the heart H to connect the blood pump assembly 100 to the heart H. The second outer wall 108 of the housing 104 has a chamfered edge 109 to avoid irritating other tissue that may come into contact with the blood pump assembly 100, such as the patient's diaphragm.

The blood pump assembly 100 further includes a stator 112, a rotor 114, and an on-board controller 116, all of which are enclosed within the pump housing 104. In the illustrated embodiment, the stator 112 and the on-board controller 116 are positioned on the inflow side of the pump housing 104 toward the first outer wall 106, and the rotor 114 is positioned along the second outer wall 108. In other embodiments, the stator 112, the rotor 114, and the on-board controller 116 may be positioned at any suitable location within the pump housing 104 that enables the blood pump assembly 100 to function as described herein. Power is supplied to operational components of the blood pump assembly 100 (e.g., the stator 112 and the on-board controller 116) from a remote power supply via a power supply cable 120.

With additional reference to FIG. 4, the pump housing 104 defines an inlet 122 for receiving blood from a ventricle of a heart (e.g., left ventricle LV), an outlet 124 for returning blood to a circulatory system, and a flow path 126 extending from the inlet 122 to the outlet 124. The pump housing 104 further defines an internal compartment 128 separated from the flow path 126, for example, by one or more dividing walls 130. The pump housing 104 also includes an intermediate wall 132 located between the first outer wall 106 and the second outer wall 108, and a peripheral wall 134 that extends between the first outer wall 106 and the intermediate wall 132. Together, the first outer wall 106, the dividing wall 130, the intermediate wall 132, and the peripheral wall 134 define the internal compartment 128 in which the stator 112 and the on-board controller 116 are enclosed.

In the illustrated embodiment, the pump housing 104 also includes a cap 136 removably attached to the pump housing 104 along the intermediate wall 132. The cap 136 is threadably connected to the pump housing 104 in the illustrated embodiment, although in other embodiments the cap 136 may be connected to the pump housing 104 using any suitable connection means that enables the blood pump assembly 100 to function as described herein. In some embodiments, for example, the cap 136 is non-removably connected to the pump housing 104, for example, by welding. The removable cap 136 includes the second outer wall 108, the chamfered edge 109, and defines the outlet 124. The cap 136 also defines a volute 138 that is in fluid communication with the outlet 124, and a rotor chamber 140 in which the rotor 114 is positioned. The cap 136 can be attached to the pump housing 104 using any suitable connection structure. For example, the cap 136 can be engaged via threads with the peripheral wall 134 to seal the cap 136 in engagement with the peripheral wall 134.

The rotor 114 is positioned within the blood flow path 126, specifically, within the rotor chamber 140, and is operable to rotate in response to an electromagnetic field generated by the stator 112 to pump blood from the inlet 122 to the outlet 124. The rotor defines a central aperture 142 through which blood flows during operation of the blood pump 102. The rotor 114 includes impeller blades 144 located within the volute 138 of the blood flow path 126, and a shroud 146 that covers the ends of the impeller blades 144 facing the second outer wall 108 to assist in directing blood flow into the volute 138.

In the illustrated embodiment, the rotor 114 includes a permanent magnet 148 that defines the central aperture 142. The permanent magnet 148 has a permanent magnetic north pole N and a permanent magnetic south pole S for combined active and passive magnetic levitation of the rotor 114 and for rotation of the rotor 114. In operation, the stator 112 is controlled to drive (i.e., rotate) the rotor and to radially levitate the rotor 114 by generating electromagnetic fields that interact with the permanent magnetic poles S and N of the permanent magnet 148.

Any suitable stator 112 can be employed to rotate the rotor 114. The stator 112 generally includes a plurality of winding structures that generate suitable electromagnetic fields that interact with the rotor 114 to cause rotor 114 to rotate and levitate. In the illustrated embodiment, the stator 112 includes a plurality of pole pieces 150 arranged circumferentially at intervals around the dividing wall 130. The example blood pump assembly 100 includes six pole pieces 150, two of which are visible in FIG. 4. In other embodiments, the blood pump assembly 100 can include more than or less than six pole pieces, such as four pole pieces, eight pole pieces, or any other suitable number of pole pieces that enables the blood pump assembly 100 to function as described herein. In the illustrated embodiment, each of the pole pieces 150 includes a drive coil 152 for generating an electromagnetic field to rotate the rotor 114, and a levitation coil 154 for generating an electromagnetic field to control the radial position of the rotor 114.

Each of the drive coils 152 and the levitation coils 154 includes multiple windings of a conductor wound around the pole pieces 150. The drive coils 152 and the levitation coils 154 of the stator 112 are arranged in opposing pairs and are controlled to drive the rotor and to radially levitate the rotor 114 by generating electromagnetic fields that interact with the permanent magnetic poles S and N of the permanent magnet 148. Suitable methods for controlling the stator 112 and generating electromagnetic fields to rotate and radially levitate the rotor 114 are described, for example, in U.S. Pat. No. 9,849,224, the entire contents of which are incorporated herein by reference for all purposes. Although the drive coil 152 and levitation coil 154 are shown as separate coils in the illustrated embodiment, it should be understood that the drive coil 152 and levitation coil 154 may be implemented as a single coil configured to generate electromagnetic fields for both rotating and radially levitating the rotor 114.

The inflow cannula 110 is attached to the pump housing 104 at the inlet 122. The pump housing 104 includes suitable connecting structure at the inlet 122 for connecting the inflow cannula 110 to the pump housing 104. In some embodiments, for example, the pump housing 104 includes a threaded sleeve that threadably engages threads on a downstream or proximal end of the inflow cannula 110 to connect the inflow cannula 110 to the pump housing 104.

The on-board controller 116 is operatively connected to the stator 112, and is configured to control operation of the pump 102 by controlling the supply of electrical current to the stator 112 and thereby control rotation of the rotor 114. In some embodiments, the on-board controller 116 is configured to perform closed-loop speed control of the pump rotor 114 based on feedback received from one or more sensors (e.g., pressure sensors, flow sensors, accelerometers, etc.) included within the blood pump assembly 100. The on-board controller 116 can be configured to control the rotor 114 in continuous flow operation and/or pulsatile flow operation.

The on-board controller 116 can include one or more modules or devices that are enclosed within pump housing 104. The on-board controller 116 can generally include any suitable computer and/or other processing unit, including any suitable combination of computers, processing units and/or the like that may be communicatively coupled to one another (e.g., on-board controller 116 can form all or part of a controller network). Thus, on-board controller 116 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit (ASIC), a digital signal processor (DSP), a field programmable gate array (FPGA), and other programmable circuits. Additionally, the memory device(s) of on-board controller 116 may generally include memory element(s) including, but not limited to, non-transitory computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the on-board controller 116 to perform various functions including, but not limited to, controlling the supply of electrical current to the stator 112, adjusting the speed of the rotor 114, and various other suitable computer-implemented functions.

In the illustrated embodiment, the on-board controller 116 is implemented as one or more circuit boards 156 and various components carried on the circuit boards (e.g., processors and memory devices) to control operation of the pump 102 by controlling the electrical supply to the stator 112.

A communication line (e.g., communication line 28) couples the blood pump assembly 100 and on-board controller 116 to the external system controller 22, which monitors system operation via various software applications. The blood pump assembly 100 itself may also include several software applications that are executable by the on-board controller 116 for various functions, such as to control radial levitation and/or drive of the rotor 114 of the pump assembly 100 during operation. The external system controller 22 can in turn be coupled to batteries 24 or a power module (not shown) that connects to an AC electrical outlet. The external system controller 22 can also include an emergency backup battery (EBB) to power the system (e.g., when the batteries 24 are depleted) and a membrane overlay, including Bluetooth capabilities for wireless data communication. An external computer that is configurable by an operator, such as clinician or patient, can further be coupled to the circulatory support system 10 for configuring the external system controller 22, the implanted blood pump assembly 100, and/or patient specific parameters, updating software on the external system controller 22 and/or the implanted blood pump assembly 100, monitoring system operation, and/or as a conduit for system inputs or outputs.

Figure 5:
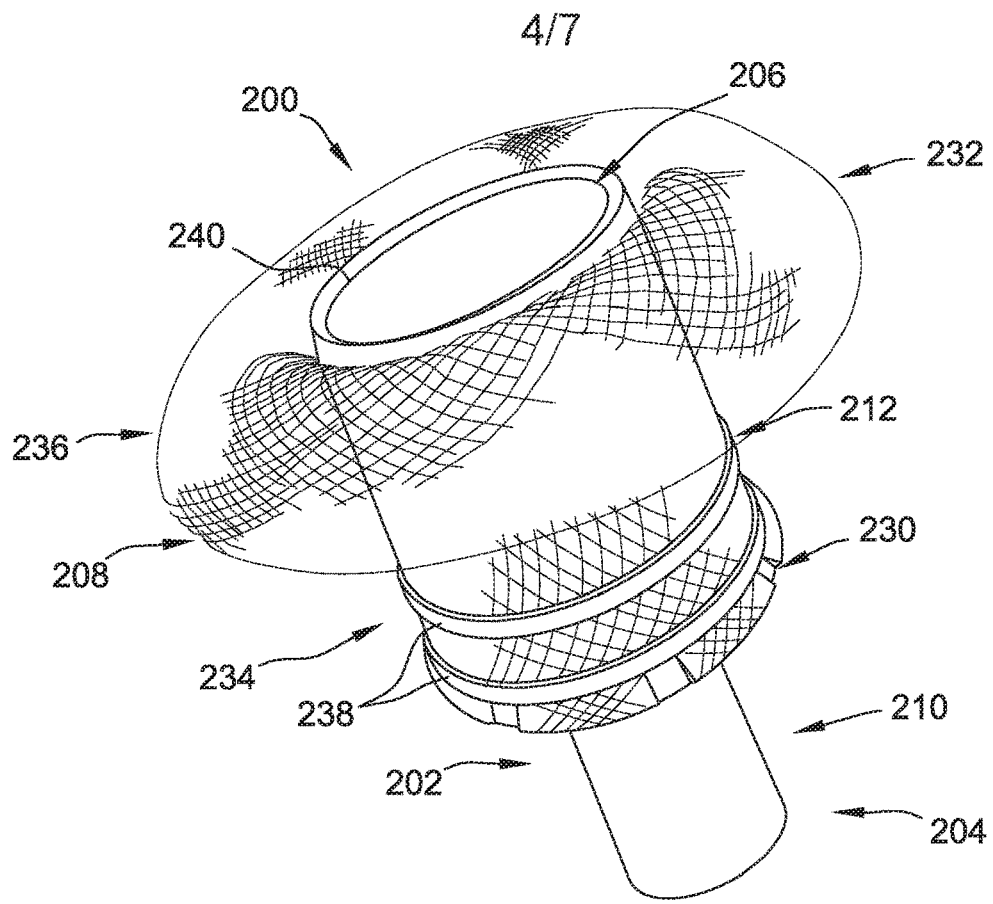
FIG. 5 is a perspective view of one exemplary embodiment of an inflow cannula suitable for use with the blood pump assembly of FIG. 3, where the inflow cannula includes an expandable sleeve shown in a deployed configuration.
Figure 6:
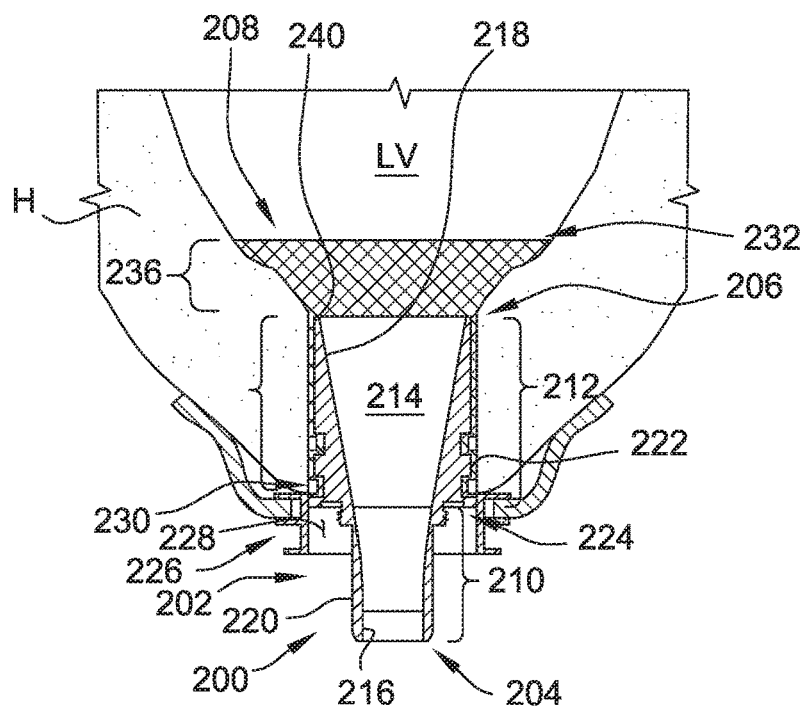
FIG. 6 is a sectional view of the inflow cannula of FIG. 5 implanted in a patient's heart, where the expandable sleeve is shown in the deployed configuration.

FIG. 5 is a perspective view of one exemplary embodiment of an inflow cannula 200 suitable for use with the blood pump assembly 100 of FIG. 3 and the circulatory support system 10 of FIG. 1. FIG. 6 is a sectional view of the inflow cannula 200 implanted in a patient's heart H. The inflow cannula 200 includes a tubular body 202 extending from a proximal end 204 to a distal end 206, and an expandable tubular sleeve 208 coupled to the body 202. As described further herein, the sleeve 208 is configured to occupy potential areas of low blood flow or stasis around the inflow cannula 200, and thereby reduce or alleviate problems associated with prothrombotic regions of the heart H following implantation of the blood pump assembly 100.

The cannula body 202 includes a proximal portion 210 adapted for connection to a pump housing, such as the pump housing 104, and a distal portion 212 adapted for positioning within an opening or hole formed in the heart H, as shown in FIG. 6. That is, the distal portion 212 is sized and shaped to be received within a cored hole formed in the heart H. When the inflow cannula 200 is implanted in a patient, the distal portion 212 passes through an opening formed in the heart H. When the blood pump assembly is fully implanted into a patient, as shown in FIGS. 1 and 3 for example, the proximal portion 210 is coupled to and/or housed within the pump housing 104.

The proximal portion 210 has an outer diameter smaller than an outer diameter of the distal portion 212 in the illustrated embodiment. Further, in the illustrated embodiment, each of the proximal portion 210 and the distal portion 212 are cylindrical, although in other embodiments, one or both of the proximal portion 210 and the distal portion 212 may be shaped other than cylindrical.

As shown in FIG. 6, the inflow cannula 200 defines a flow path 214 for supplying blood from within a ventricle of the heart H (shown as the left ventricle LV in FIG. 6) to the inlet 122 of the pump housing 104 (both shown in FIG. 4). In the illustrated embodiment, the flow path 214 tapers radially inward from the distal end 206 of the cannula body 202 to the proximal end 204 of the cannula body 202 to form a reduced cross-sectional area along the proximal portion 210.

The proximal portion 210 and the distal portion 212 of the cannula body 202 include respective inner surfaces 216, 218 that define the flow path 214, and respective exterior surfaces 220, 222.

The proximal portion 210 includes a suitable coupler 224 for coupling to the pump housing 104. Suitable couplers include, for example and without limitation, threads, snap-fit couplers, quick-connect couplers, and cuff-locking mechanisms. In the illustrated embodiment, the coupler 224 is shown as external threads along the proximal portion 210 of the inflow cannula 200.

In some embodiments, the inflow cannula 200 is coupled or otherwise secured to the heart H by a ventricular cuff 226, shown in FIG. 6. The cuff 226 defines an opening 228 that receives the inflow cannula 200 therein. The cuff 226 includes a suitable coupler (e.g., a clamp (not shown in FIG. 6)) that couples the cuff 226 to the inflow cannula 200. The cuff 226 may also include a locking mechanism (e.g., a cam (not shown in FIG. 6)) that secures the coupler in a closed position, thereby limiting the possibility of the cuff 226 accidentally becoming uncoupled from the inflow cannula 200. In some embodiments, the cuff 226 may include a separate coupler for coupling the cuff 226 to the pump housing 104.

In some embodiments, the ventricular cuff 226 is coupled to the heart H (e.g., using sutures) following a coring process that forms a hole in the patient's heart H. Further, in some embodiments, the inflow cannula 200 is positioned within and coupled to the heart H (e.g., via the ventricular cuff 226) after the cuff 226 is coupled to the heart H.

It should be understood that the inflow cannula 200 and ventricular cuff 226 may have other suitable configurations without departing from some aspects of the present disclosure. Other configurations of inflow cannulas and ventricular cuffs, and techniques for coupling inflow cannulas and ventricular cuffs to a patient's heart, suitable for use with certain aspects of the present disclosure are described, for example, in U.S. Pat. No. 9,981,076, the entire contents of which are incorporated herein by reference for all purposes.

The sleeve 208 is coupled to the exterior surface 222 of the distal portion 212, and is configured to expand from a first, stored configuration (shown in FIG. 7) to a second, deployed configuration (shown in FIGS. 5 and 6) to occupy a volume around (i.e., radially outward from) the distal portion 212 of the cannula body 202, and thereby fill or occupy areas of potential stasis around the distal portion 212 of the cannula body 202. More specifically, in the illustrated embodiment, the sleeve 208 extends from a proximal end 230 coupled to the cannula body 202 to a free, distal end 232, and includes a first portion 234 coupled to the distal portion 212 of the cannula body 202, and a second portion 236 extending from the distal end 206 of the cannula body 202. The second portion 236 is deployable from the stored configuration to the deployed configuration in which the second portion 236 expands radially to engage and conform to an endocardial surface of the heart H. In the illustrated embodiment, for example, the second portion 236 of the sleeve 208 is not directly fixed to the cannula body 202 and is only secured to the cannula body 202 via the first portion 234 of the sleeve 208. Once deployed, the second portion 236 of the sleeve 208 is therefore free to expand and conform to surfaces surrounding the distal portion 212 of the cannula body 202, such as the endocardial surface of the heart H.

Figure 7:
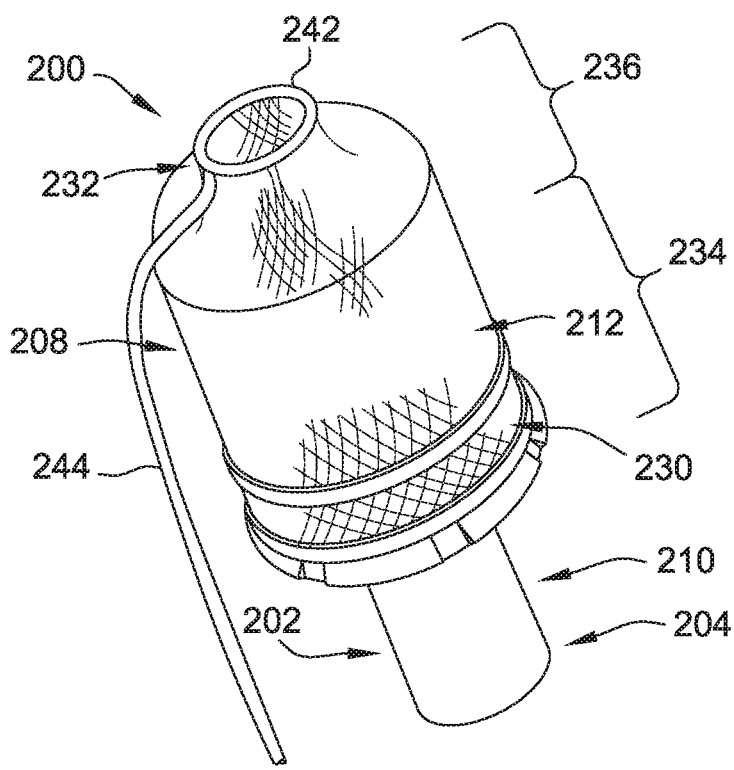
Figure 8:
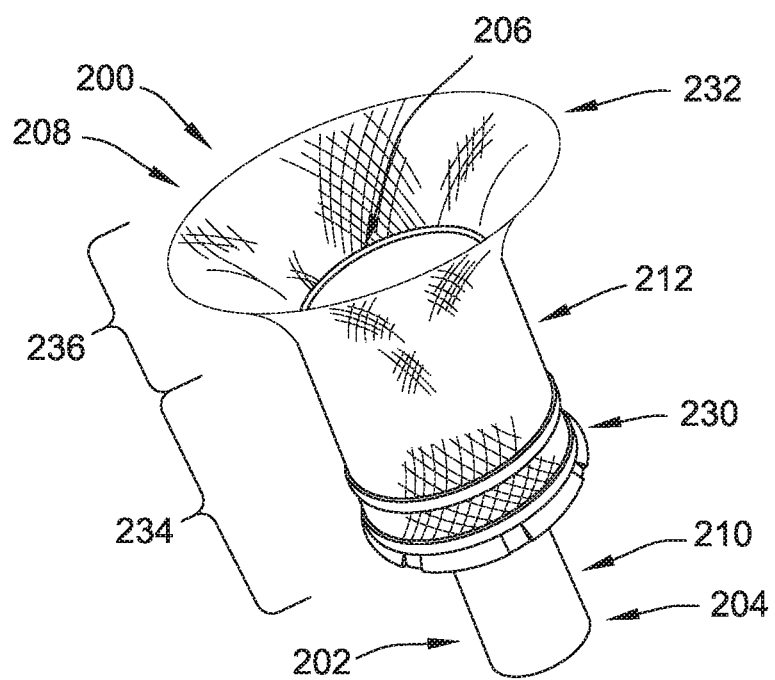

In the illustrated embodiment, the first portion 234 of the sleeve 208 is coupled to the distal portion 212 of the cannula body 202 by a plurality of crimp rings 238. Two crimp rings 238 are shown in FIG. 5, although the sleeve 208 may be coupled to the cannula body 202 using any suitable number of crimp rings, including more than or less than two. Further, in the illustrated embodiment, the sleeve 208 is fixed to a distal tip 240 of the cannula body 202 along the first portion 234 of the sleeve 208 such that the first portion 234 of the sleeve 208 maintains engagement with the distal portion 212 of the cannula body 202 when the sleeve 208 is in the deployed configuration. Additionally, because the sleeve 208 is fixed to the distal tip 240 of the cannula body 202 along the first portion 234 of the sleeve 208, the second portion 236 of the sleeve 208 unfolds about the distal tip 240 of the cannula body 202 when the sleeve 208 is deployed from the stored configuration to the deployed configuration, as illustrated in FIGS. 7-9. In other embodiments, the sleeve 208 may be coupled to the cannula body 202 using any suitable couplers or fasteners that enable the sleeve 208 to function as described herein.

In the stored configuration, shown in FIG. 7, the second portion 236 of the sleeve 208 has a smaller diameter than the first portion 234 of the sleeve 208 and the distal portion 212 of the cannula body 202. The diameter of the second portion 236 of the sleeve 208 in the stored configuration is also smaller than the diameter of the second portion 236 in the deployed configuration. Prior to delivery and implanting the inflow cannula 200 in the heart H, the second portion 236 of the sleeve 208 can be maintained in the stored configuration to facilitate insertion of the inflow cannula 200 through the hole formed in the heart H. Once the inflow cannula 200 is inserted through the hole and secured or coupled to the heart H, the second portion of the sleeve 208 can be deployed to the deployed configuration.

With reference to FIG. 7, a retainer 242 is coupled to the distal end 232 of the sleeve 208 to maintain the sleeve 208 in the stored configuration. In the illustrated embodiment, the retainer 242 is a retaining ring that extends around the distal end 232 of the sleeve 208. In other embodiments, the retainer 242 can generally include any suitable retaining mechanism that enables the sleeve 208 to function as described herein. In some embodiments, for example, the inflow cannula 200 can include a cap fitted around the distal end 232 of the sleeve 208.

Further, in the illustrated embodiment, a release mechanism 244 is coupled to the retainer 242 and is operable to release the retainer 242 from the distal end 232 of the sleeve 208 to allow the second portion 236 of the sleeve 208 to deploy from the stored configuration to the deployed configuration. In the illustrated embodiment, the release mechanism 244 is shown disposed outside of the cannula body 202 and the sleeve 208, although in other embodiments, the release mechanism 244 may be disposed within the sleeve 208 and/or the cannula body 202. In one embodiment, for example, the release mechanism 244 extends from the distal end 232 of the sleeve 208, through the flow path 214 defined by the cannula body 202, and out of the proximal end 204 of the cannula body 202. In the illustrated embodiment, the release mechanism 244 is a release line constructed of a wire or thread of material, such as a suture. Further, in the illustrated embodiment, the release line is formed integrally with the retainer. That is, in the illustrated embodiment, the retainer 242 and release mechanism 244 are constructed of a continuous wire or thread of material, such as a suture. In other embodiments, such as embodiments including a retaining cap, the release mechanism 244 may include an elongate object or tool that extends through the cannula flow path 214 and the sleeve 208 to push the retainer 242 up off of the sleeve 208 and, after the sleeve 208 is deployed, pull the retainer 242 back through the flow path 214 defined by the cannula body 202.

In its pre-implant state, the expandable sleeve 208 is gathered together with the retainer 242 (e.g., a suture ring) and maintained in the stored configuration such that the sleeve 208 can fit through a cored hole in the myocardium of the heart H. To implant the inflow cannula 200, the inflow cannula 200 is inserted through the cored hole and secured to the heart H, for example, via the ventricular cuff 226. In some embodiments, the ventricular cuff 226 and inflow cannula 200 are pre-assembled and implanted together, i.e., as a single unit. In other embodiments, the ventricular cuff and inflow cannula 200 are implanted separately, i.e., in a sequence. The ventricular cuff 226 is attached to the heart using suitable attachment means (e.g., sutures). Once the inflow cannula 200 is secured to the heart (e.g., after the ventricular cuff 226 is sutured to the heart), the release mechanism 244 is activated to deploy the sleeve 208 from the stored configuration to the deployed configuration, allowing the sleeve to expand and relax, and conform to the ventricle walls of the heart H. Once the sleeve 208 is deployed, the pump housing 104 can be connected to the inflow cannula 200 (specifically, the proximal portion 210 of the cannula body 202) and/or the ventricular cuff 226. When the pump 102 is activated and the ventricle refills with blood, the sleeve 208 will block blood flow from between the sleeve 208 and the myocardial walls, forming a stationary thrombus that will eventually be covered in re-endothelialized tissue, and never released into the blood stream. Tissue reendothelialization may occur within 30 days following the implant procedure.

With additional reference to FIG. 10, the sleeve 208 includes a sidewall 246 that includes an outer layer 248 and an inner layer 250. In this embodiment, the sidewall 246 is formed by folding a mesh material over onto itself. Accordingly, the sidewall 246 includes an outer mesh layer 248 and an inner mesh layer 250 joined to the outer mesh layer 248 at a distal tip 252 of the sleeve 208. In other embodiments, the sidewall 246 may be formed using any other suitable method that enables the sleeve 208 to function as described herein.

As shown in FIG. 10, the inner layer 250 is spaced from the outer layer 248 by a spacing 254. The size of the spacing 254 illustrated in FIG. 10 is exaggerated for illustrative purposes. In practice, when the sleeve 208 is in the stored configuration, the spacing 254 may be significantly smaller than is shown in FIG. 10, and may even be zero (i.e., the inner layer 250 is in contact with the outer layer 248). As shown in FIG. 12, the inner layer 250 and outer layer 248 are not joined or fixed to one another along the second portion 236 of the sleeve 208, other than at the distal tip 252. Accordingly, the spacing 254 between the inner layer 250 and the outer layer 248 is permitted to increase or expand when the sleeve 208 is deployed from the stored configuration to the deployed configuration as shown in FIG. 12) to facilitate filling potential areas of low blood flow or stasis around the distal portion 212 of the cannula body 202. Stated another way, a thickness of the sidewall 246, measured from the outer layer 248 to the inner layer 250, may increase when the second portion 236 of the sleeve 208 is deployed from the stored configuration to the deployed configuration.

In some embodiments, the sidewall thickness or spacing 254 between the inner layer 250 and outer layer 248 may not change significantly when the sleeve 208 is deployed. As shown in FIG. 6, for example, where heart tissue is disposed above the distal tip 240 of the cannula body 202, the second portion 236 of the sleeve 208 stops expanding when the sleeve 208 contacts the heart tissue, and the outer layer 248 and the inner layer 250 may remain in contact with one another. In other embodiments, for example, where the distal portion 212 of the cannula body 202 protrudes a distance into the ventricle of the heart H and the distal tip 240 is spaced above the heart tissue, the second portion 236 of the sleeve 208 may fold over and backward behind the distal tip 240 of the cannula body 202. In such embodiments, the sidewall thickness or spacing 254 between the outer layer 248 and the inner layer 250 may increase to facilitate filling potential areas of low blood flow or stasis.

The sleeve 208 has a suitably flexible construction to allow the sleeve 208 (specifically, the second portion 236 of the sleeve 208) to expand from the stored configuration and substantially conform and engage endocardial surfaces of the heart H surrounding the distal portion 212 of the inflow cannula 200. Moreover, the sleeve 208 has sufficient resiliency to ensure the sleeve (specifically, the second portion 236 of the sleeve) substantially expands back to the deployed configuration when deployed (e.g., once the retainer 242 is released from the distal end 232 of the sleeve 208).

In the illustrated embodiment, the sleeve 208 has a mesh construction formed from a network of intertwined wires or threads to provide suitable flexibility and resiliency. That is, the sleeve 208 is constructed of a tubular mesh. More specifically, in the illustrated embodiment, the sleeve 208 is constructed of a braided wire, although in other embodiments, the sleeve 208 may have a construction other than a braided wire. Further, in some embodiments, the sleeve 208 is constructed from one or more super elastic materials and/or shape-memory materials. A super-elastic material exhibits pseudo-elastic recovery or "memory" from one shape to another multiple times upon the application and release of deforming stress or force. A small stress or force may induce considerable deformation, but the material or component including such a material recovers its original shape when the deforming force or stress is released. Shape-memory materials are materials that have the ability to "memorize" or retain a previous or initial shape or configuration when subjected to certain stimuli, such as stress or heat. Accordingly, in some embodiments, the sleeve 208 has shape memory properties that, when activated, bias or force the sleeve 208 towards the deployed configuration. In such embodiments, the shape-memory material may be activated by heat (e.g., from a patient's heart or other heat source), and force or bias the sleeve 208 back to its original or deployed configuration to facilitate full deployment of the sleeve 208.

Suitable super elastic and shape-memory materials from which the sleeve 208 can be constructed include, for example and without limitation, nickel-titanium alloys (i.e., nitinol) and polymers. In one particular embodiment, the sleeve 208 is constructed of a nitinol braid that includes a plurality of intertwined nitinol wires or a single nitinol wire intertwined with itself to form a braided sleeve. Braided nitinol has a demonstrated ability to stop the passage of blood and to promote reendothelialization, which facilitates passivating the area and developing a more hemocompatible environment at the pump-tissue interface.

The thickness or diameter of the wires used to construct the sleeve 208 may be varied according to a desired stiffness of the sleeve 208. For example, a thicker wire may be used to provide a stiffer construction of the sleeve 208, whereas a thinner wire may be used to provide a more flexible construction of the sleeve 208. In some particular embodiments, the sleeve 208 is constructed of braided nitinol wire, and the wires have a thickness or diameter in the range of 0.01 millimeters to 0.50 millimeters. In other embodiments, the wires may have any suitable thickness or diameter that enables the sleeve 208 to function as described herein.

Moreover, in some embodiments, the sleeve 208 may have a variable stiffness from the proximal end 230 to the distal end 232. For example, a thickness of the wire may vary along a length of the sleeve 208 to provide stiffer regions and more flexible regions along the length of the sleeve 208. Additionally or alternatively, the sleeve 208 may include one or more structural reinforcing members to selectively increase the stiffness of the sleeve 208 at desired locations along the length of the sleeve 208. In one particular implementation, the first portion 234 of the sleeve 208 has a stiffer construction than the second portion 236 of the sleeve 208.

In some embodiments, the sleeve 208 may include one or more layers that promotes reendothelialization and/or reduced blood flow. By way of example, the outer layer 248 and/or the inner layer 250 may be formed of and/or may include a material (e.g., a coating, a patch, etc.) that promotes reendothelialization and/or reduced blood flow in the area adjacent the respective layer. In some embodiments, for example, one or both of the outer layer 248 and the inner layer 250 include a polyester patch that promotes reendothelialization and reduced blood flow in the area adjacent the respective layers.

Figure 11:
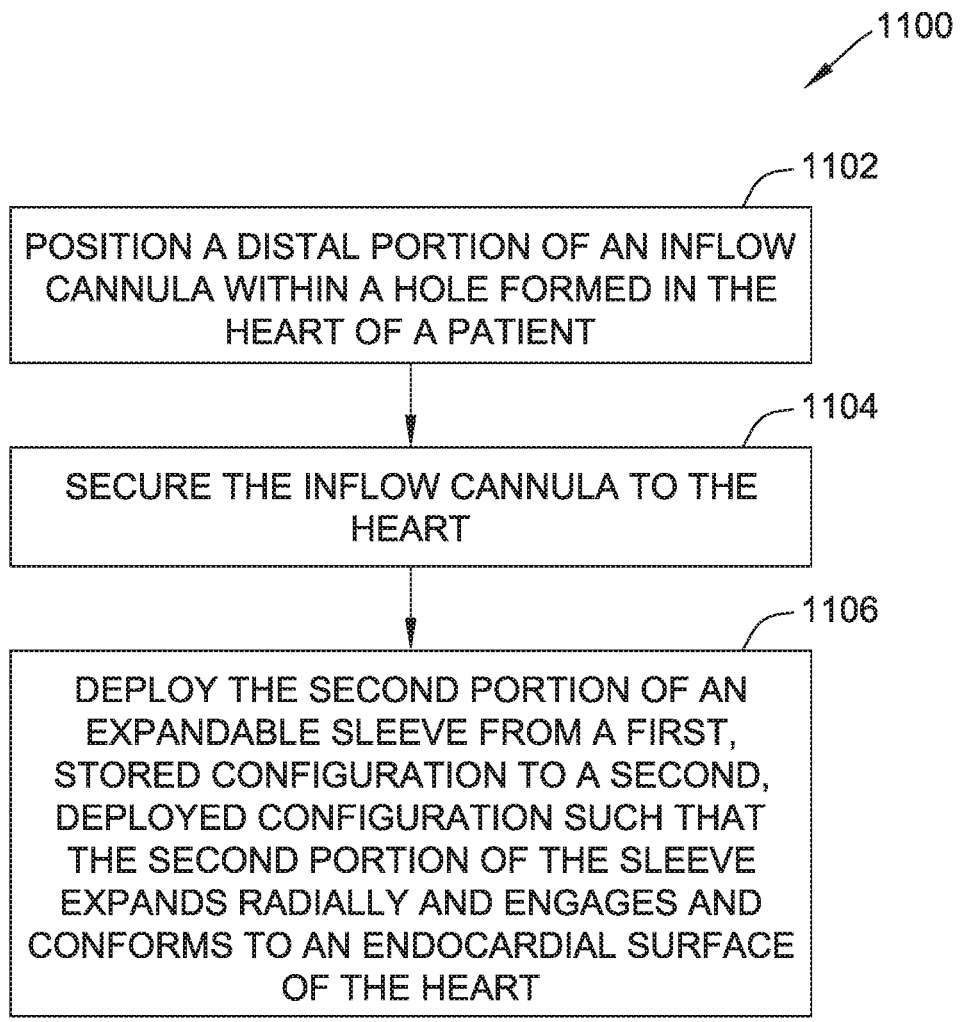
FIG. 11 is a flow diagram illustrating one embodiment of a method for implanting an inflow cannula within a heart of a patient.

FIG. 11 is a flow diagram illustrating one embodiment of a method 1100 for implanting an inflow cannula, such as the inflow cannula 200, within a heart of a patient. In the illustrated embodiment, the method 1100 includes positioning 1102 a distal portion of the inflow cannula within a hole formed in the heart. The inflow cannula includes an expandable sleeve, such as the expandable sleeve 208, having a first portion coupled to the distal portion of the inflow cannula and a second portion extending from a distal end of the inflow cannula. The method 1100 further includes securing 1104 the inflow cannula to the heart, and deploying 1106 the second portion of the sleeve from a first, stored configuration to a second, deployed configuration such that the second portion of the sleeve expands radially and engages and conforms to an endocardial surface of the heart.

In some embodiments, deploying 1106 the sleeve includes deploying the sleeve subsequent to the inflow cannula being secured to the heart. That is, the sleeve is deployed only after the inflow cannula is secured to the heart. Further, in some embodiments, deploying 1106 the sleeve includes releasing a retainer, such as retainer 242, coupled to a distal end of the sleeve. In some embodiments, the retainer is a retaining ring. In such embodiments, releasing the retainer can include applying tension to a release line that is coupled to the retaining ring, and that extends from the distal end of the sleeve, through a flow path defined by the inflow cannula, and out of a proximal end of the cannula.

In some embodiments, the method 1100 further includes attaching a ventricular cuff to the heart. In such embodiments, the inflow cannula can be secured to the heart by the ventricular cuff. In some embodiments, the ventricular cuff defines a central opening, and positioning 1102 a distal portion of the inflow cannula within the hole formed in the heart includes inserting the distal portion of the inflow cannula through the central opening defined by the ventricular cuff. Further, in such embodiments, securing the inflow cannula to the heart can include coupling the inflow cannula to the ventricular cuff.

In some embodiments, the method 1100 further includes connecting the inlet cannula to a blood pump assembly, such as the blood pump assembly 100. In some embodiments, for example, the method 1100 includes coupling a proximal portion of the inflow cannula to a pump housing of the blood pump assembly. Additionally, the method 1100 can include coupling the pump housing to a ventricular cuff attached to the heart.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An inflow cannula for an implantable blood pump assembly, said inflow cannula comprising:
   a tubular body extending from a proximal end to a distal end, the tubular body comprising a proximal portion adapted for connection to a pump housing, and a distal portion adapted for positioning within an opening formed in a heart; and
   an expandable sleeve comprising a tubular mesh having an outer layer and an inner layer, the sleeve coupled to an exterior surface of the distal portion and having a first portion coupled to the distal portion of the tubular body and a second portion extending from the distal end of the tubular body, wherein the second portion is deployable from a first, stored configuration to a second, deployed configuration in which the second portion expands radially to engage and conform to an endocardial surface of the heart.

2. The inflow cannula of claim 1, wherein the sleeve is fixed to a distal tip of the tubular body along the first portion of the sleeve such that the first portion of the sleeve maintains engagement with the distal portion of the tubular body when the sleeve is in the deployed configuration, and such that the second portion of the sleeve unfolds about the distal tip of the tubular body when the sleeve is deployed from the stored configuration to the deployed configuration.

3. The inflow cannula of claim 1, wherein the inner layer of the sleeve is joined to the outer layer of the sleeve at a distal tip of the sleeve.

4. The inflow cannula of claim 3, wherein a spacing between the inner layer and the outer layer is permitted to increase when the sleeve is deployed from the stored configuration to the deployed configuration.

5. The inflow cannula of claim 1, wherein the sleeve extends from a proximal end coupled to the tubular body to a free, distal end, wherein the inflow cannula further comprises a retainer coupled to the sleeve distal end, wherein the retainer maintains the sleeve in the stored configuration.

6. The inflow cannula of claim 5, further comprising a release mechanism coupled to the retainer and operable to release the retainer from the sleeve distal end to allow the second portion of the sleeve to deploy from the stored configuration to the deployed configuration.

7. The inflow cannula of claim 6, wherein the release mechanism extends from the sleeve distal end, through a flow path defined by the tubular body, and out of the proximal end of the tubular body.

8. The inflow cannula of claim 6, wherein the retainer comprises a retaining ring, wherein the release mechanism comprises a release line, and wherein the retaining ring is formed integrally with the release line.

9. The inflow cannula of claim 1, wherein the first portion of the sleeve is coupled to the distal portion of the tubular body by at least one crimp ring.

10. The inflow cannula of claim 1, wherein the sleeve comprises a braided nickel-titanium alloy.

11. An implantable blood pump assembly comprising:
    a housing defining an inlet, an outlet, and a flow path extending from the inlet to the outlet;
    a rotor positioned within the flow path and operable to pump blood from the inlet to the outlet;
    a stator positioned within the pump housing and operable to drive the rotor;
    an inflow cannula having a proximal portion adapted for coupling to the housing inlet and a distal portion opposite the proximal portion; and
    an expandable sleeve comprising a tubular mesh having an outer layer and an inner layer, the sleeve coupled to an exterior of the distal portion and having a first portion coupled to the distal portion of the inflow cannula and a second portion extending from a distal end of the inflow cannula, wherein the second portion is deployable from a first, stored configuration to a second, deployed configuration in which the second portion expands radially to engage and conform to an endocardial surface of a heart.

12. The implantable blood pump assembly of claim 11, wherein the sleeve comprises a braided nickel-titanium alloy, wherein the sleeve extends from a proximal end coupled to the inflow cannula to a free, distal end, wherein a retainer is coupled to the sleeve distal end and maintains the sleeve in the stored configuration, and wherein the sleeve is fixed to a distal tip of the inflow cannula along the first portion of the sleeve such that the first portion of the sleeve maintains engagement with the distal portion of the inflow cannula when the sleeve is in the deployed configuration, and such that the second portion of the sleeve unfolds about the distal tip of the inflow cannula when the sleeve is deployed from the stored configuration to the deployed configuration.

13. A method for implanting an inflow cannula within a heart of a patient, the method comprising:
  positioning a distal portion of the inflow cannula within a hole formed in the heart, wherein the inflow cannula includes an expandable sleeve comprising a tubular mesh having an outer layer and an inner layer, the sleeve having a first portion coupled to the distal portion of the inflow cannula and a second portion extending from a distal end of the inflow cannula;
  securing the inflow cannula to the heart; and
  deploying the second portion of the sleeve from a first, stored configuration to a second, deployed configuration such that the second portion of the sleeve expands radially and engages and conforms to an endocardial surface of the heart.

14. The method of claim 13, wherein deploying the sleeve comprises releasing a retainer coupled to a distal end of the sleeve.

15. The method of claim 14, wherein the retainer is a retaining ring, and wherein releasing the retainer comprises applying tension to a release line coupled to the retaining ring, wherein the release line extends from the distal end of the sleeve, through a flow path defined by the inflow cannula, and out of a proximal end of the inflow cannula.

16. The method of claim 13, further comprising attaching a ventricular cuff to the heart, wherein the inflow cannula is secured to the heart by the ventricular cuff.

17. The method of claim 16, wherein the ventricular cuff defines a central opening, wherein positioning a distal portion of an inflow cannula within a hole formed in the heart comprises inserting the distal portion of the inflow cannula through the central opening defined by the ventricular cuff, and wherein securing the inflow cannula to the heart comprises coupling the inflow cannula to the ventricular cuff.

18. The method of claim 13, wherein deploying the sleeve comprises deploying the sleeve subsequent to the inflow cannula being secured to the heart.

19. The method of claim 13, further comprising coupling a proximal portion of the inflow cannula to a pump housing.

* * * * *